United States Patent [19]

Steigerwald et al.

[11] Patent Number: 4,728,324
[45] Date of Patent: Mar. 1, 1988

[54] URINE METER VALVE WITH TAMPER INDICATOR

[75] Inventors: Carl J. Steigerwald, Fox River Grove; Terry N. Layton, Arlington Heights, both of Ill.

[73] Assignee: The Kendall Company, Boston, Mass.

[21] Appl. No.: 919,290

[22] Filed: Oct. 15, 1986

[51] Int. Cl.$^4$ ............................................... A61M 1/00
[52] U.S. Cl. ..................................... 604/323; 128/766; 604/335; 604/318; 251/7
[58] Field of Search ..................... 604/33, 34, 322–325, 604/335, 350, 91, 110, 111, 318; 116/200, 277; 137/553; 251/4, 7; 128/200.19, 760, 762, 764, 766, 767, 771

[56] References Cited

U.S. PATENT DOCUMENTS

| | | | |
|---|---|---|---|
| 4,000,649 | 1/1977 | Hanifl | 128/771 |
| 4,018,224 | 4/1977 | Kurtz et al. | 604/321 |
| 4,305,403 | 12/1981 | Dunn | 604/323 |

FOREIGN PATENT DOCUMENTS 2900806  7/1980  Fed. Rep. of Germany ...... 128/771

Primary Examiner—C. Fred Rosenbaum
Assistant Examiner—J. L. Kruter
Attorney, Agent, or Firm—Donald N. Halgren

[57] ABSTRACT

A multiple sample valve assembly for a urine collection system with a valve for taking small urine samples in a safe manner. The valve also has a valve for taking large urine samples while having a frangible portion for indicating that the large sampling valve was used, so as to alert medical personnel to the possibility of contamination or infection if proper procedures are not undertaken. The element for indicating use comprises frangible panels or bands which may be disturbed by opening the valve.

13 Claims, 3 Drawing Figures

URINE METER VALVE WITH TAMPER INDICATOR

BACKGROUND OF THE INVENTION

(1) Field of the Invention

The present invention relates to a closed system urinary drainage bag, and more particularly to tamper evident drain valve arranged on a urine meter disposed on the front of an urine collection bag.

(2) PRIOR ART

Urine collection begins after catheterization of a patient, wherein urine drains from the bladder, through a catheter and drainage tube connected to the catheter, and into a urine collection system. The urine collection system generally comprises a urine bag, and a urine meter. A urine collection bag, for example, is shown in U.S. Pat. No. 4,465,484. A urine collection system with a holding chamber and a one way valve is shown in U.S. Pat. No. 4,460,362. These urine collection systems did not fully provide for metering capabilities and which permitted small samples to be taken while limiting the likelihood of retrograde infection or bacterial contamination within the metering chamber.

U.S. Pat. No. 4,305,405 shows a urine collection bag with a meter attached thereto. The meter has a sampling port thereon. The meter however fails to permit samples to be taken from the meter in such a quantity such as 30 to 40 ml. for tests for specific gravity or the like. U.S. Pat. Nos. 3,683,894 and 4,305,403 disclose valves for urine collection systems. U.S. patent application Ser. No. 780,042 discloses tamper (or use) evident means disposed on a catheter in a urinary collection system.

It is an object of the present invention to provide a urine meter with a drain valve thereon which will permit both means for taking small fresh samples such as with a syringe, while permitting larger fresh volumes to be removed from the urine source i.e., the meter, by opening of the drain valve. It is a further object of the invention to provide sampling ports which will minimize retrograde contamination of the fluid within the meter and hence within the system and ultimately the patient.

It is a further object of the present invention to provide a drain valve on a urine meter which drain valve has tamper evident means thereon so as to discourage use of the large volume drain valve for small volume usage.

BRIEF SUMMARY OF THE INVENTION

The present invention comprises a use or tamper evident valve with a combined urine output meter and a drainage bag for collecting, measuring and sampling urine output from a catheterized patient. The present invention permits small samples of fresh urine to be taken from the meter as well as permitting large samples to be taken from the meter when larger volumes of urine are required.

The urine meter comprises a receptacle having a wall defining a cavity and an opening at the top receptacle for communication with the cavity. A valve is disposed at the bottom of the meter body. A conduit is disposed through the bottom of the meter body and is in fluid communication with the valve thereat. The valve comprises a generally longitudinally extending housing having an adapter opening at its upper end into which the conduit extends. The valve has an opening at its lower end. A resilient, flexible tube is disposed within the generally longitudinal housing of the valve and is in overlapping relationship with the adapter which mates with the conduit from the bottom of the meter body. The housing for the valve, has a front side and a back side. A biased slider plunger extends through an opening in the front side of the housing and is movable transversely across the body of the valve. An opening through the slider permits the flexible conduit to pass therethrough. A pair of wall members are disposed on either side of the slider. The wall members define the opening therethrough to permit the flexible conduit to pass. A biasing means such as a spring is disposed against the front wall of the housing and a tab on the distalmost portion of the slider. The spring acts as biasing means which causes the proximal end of the slider to pinch the flexible conduit against a bracket arrangement on the housing and thus close the conduit off.

A sampling port is disposed between the slider and the body of the urine meter. An opening comprising the port is disposed in the upper half of a front portion of the valve body or housing. A septum, or rubber plug, is disposed over the opening.

The septum permits sampling of minute quantities of urine within the conduit before it reaches the shut off portion of the valve.

The back portion of the housing adjacent the proximal end of the slider unit has a frangible portion thereacross. The frangible portion includes a boss which extends inwardly into the valve which frangible portion will break from the back side of the valve when the slider has been (pushed inwardly) advanced so as to permit fluid flow therethrough. The frangible portion comprises a tamper evident means for determining use of the large sampling or drain portion of the valve.

A shrinkable tape may be disposed about the valve body to cover portions of the back of the valve housing so as to indicate tampering therewith when the valve has been opened, which could be used instead of or in addition to the frangible panel thereon.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
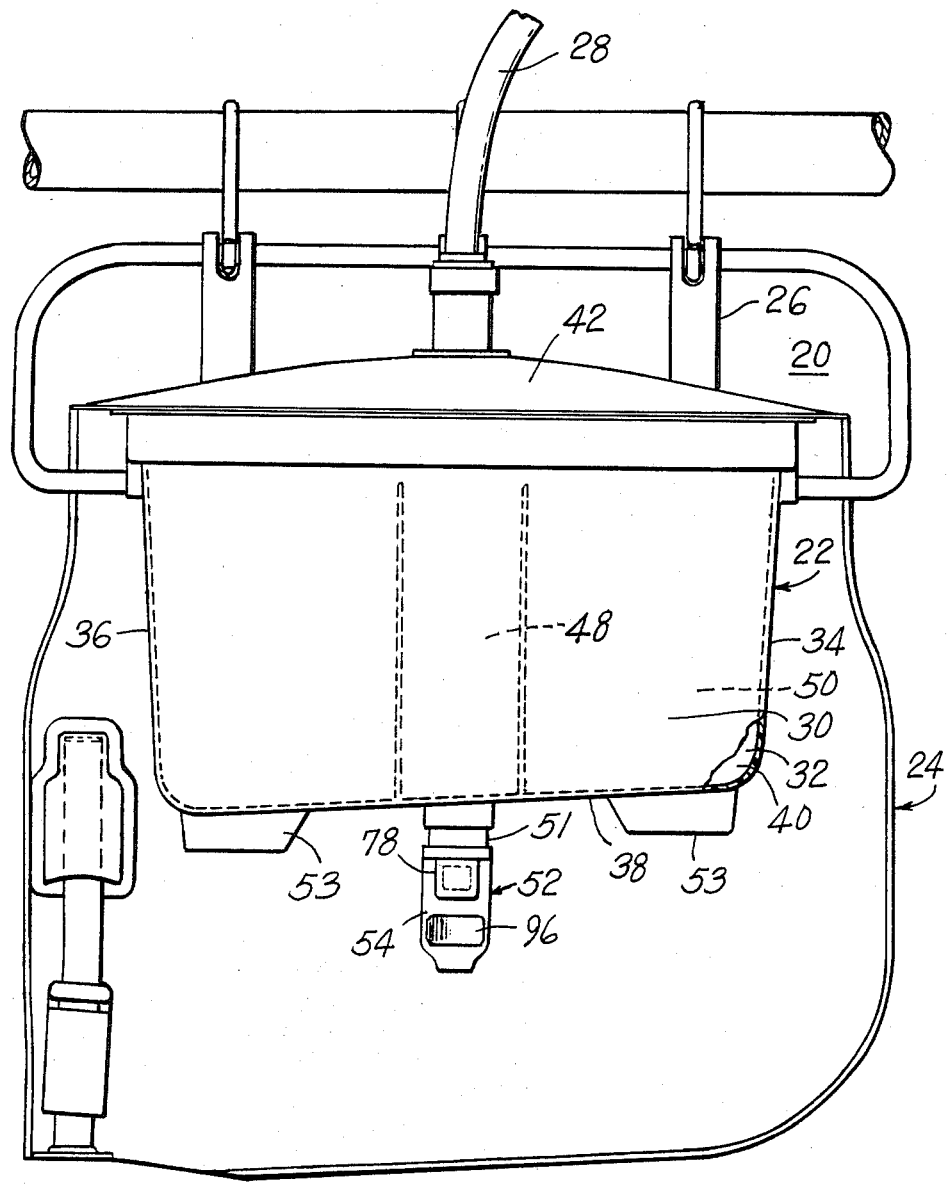
FIG. 1 is a front elevational view of a urine bag assembly having a meter therewith and a valve attached to said meter.

Referring now to the drawings in detail, and particularly to FIG. 1, there is shown a urine collection assembly 20, having a rigid front receptacle 22, a flexible rear container or bag 24, a support arrangement 26, and inlet conduit means 28, similar to that shown in commonly assigned patent application Ser. Nos. 876,622 and 919,276 both incorporated herein by reference. The receptacle 22 may be made of any suitable rigid plastic material which is transparent. The container 24 may have walls constructed of any suitable, flexible plastic material.

The receptacle 22 has a front wall 30, a rear wall 32, a pair of sidewalls 34 and 36 at proposed sides of the receptacle 22, and a bottom wall 38 defining a cavity body in the receptacle 22. The receptacle 22 has a top 42 defining an elongated opening. In use, urine is initially directed into a small inner compartment 48 for more accurate volume measurement by indicia arranged on the front wall 30. Urine is permitted to overflow from the upper portion of the walls defining the inner compartment 48. The receptacle 22 has a pair of lower depending lift tabs 53 to facilitate movement of the receptacle 22 relative to the container 24, for drainage of the contents of the receptacle 22 into the container 24.

Figure 2:
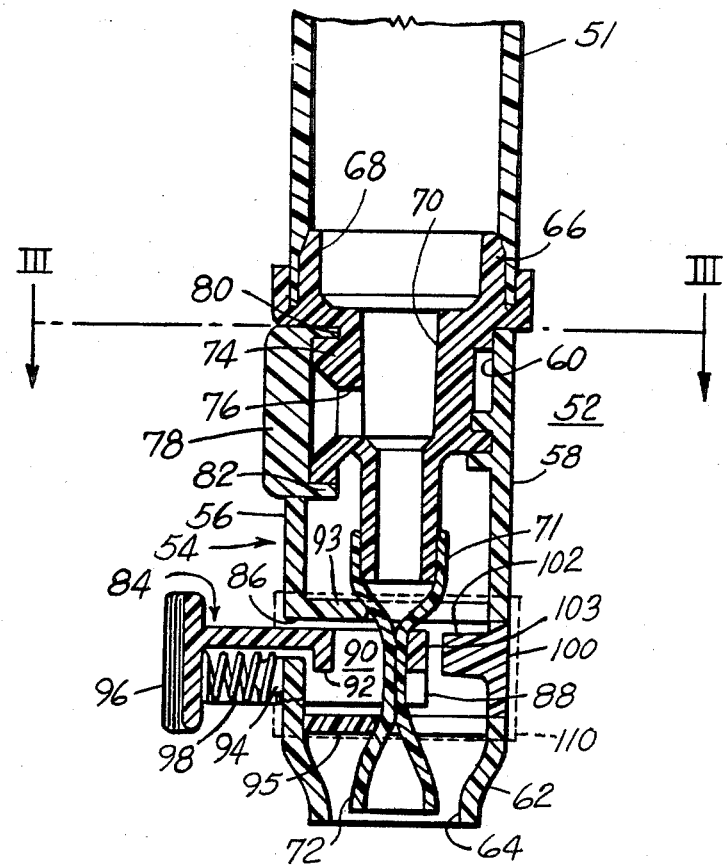
FIG. 2 is a side elevational view of the valve shown in FIG. 1.

The receptacle 22 has a lower valve 52 communicating with the inner compartment 48 through a conduit 51, as shown in FIG. 2, in order to drain urine from the inner compartment 48 during use of the urine meter 20, to obtain either a large or a small fresh sample of urine.

The valve 52 extending beneath receptacle 22 is of generally longitudinal shape, having a housing 54 comprising a front half 56, and a rear half 58. The valve 52 has an upper end with an opening 60 therein. The valve 52 has a lower end 62 with an opening 64 therein. An adapter 66 mates in the opening 60 at the upper end of the valve 52. The adapter 66 is arranged to snugly fit into the configuration of the opening 60. The uppermost distal end of the adapter 66 has a circular opening 68 theredisposed. The opening 68 in the distal end of the adapter 66 is in fluid communication with a bore 70 which extends completely longitudinally through the adapter 66. The lower end of the adapter 66 is centrally disposed within the housing 54 of the valve 52. The distalmost end of the adapter 66 has a generally cylindrically shaped configuration thereto, which mates with a flexible tubular conduit 71 which itself extends through the generally longitudinal center of the valve member 52. The flexible conduit 71 has an open end 72 which is generally coincidental with the open end of the lower end 62 of the valve 52.

The adapter 66 has a side portion 74 with an opening 76 therein. The opening 76 permits communication between the bore 70 of the adapter 66 from outside thereof.

A septum 78 made of a resilient plastic or rubber material mates over and covers the orifice 76 on the side 74 of the adapter 66, is shown in FIG. 2. The septum 78 is arranged so as to seal the opening 76 from any outside air or contamination and allows penetration by a needle or the like. An annular groove 80 around the side portion 74 on the adapter 66 receives a ridge 82 of the septum 78 to ensure the seal thereinbetween.

A slide release or slider 84 extends through an opening 86 in the front panel 56. The slider 84 is arranged transversely across the longitudinal fluid flow path in the valve 52. The slider 84 has a pair of sidewalls 88, only one shown in FIG. 2 and a pair of transverse walls 92 and 103 that extend between the sidewalls 88, which all define an opening 90 disposed therebetween. The flexible conduit or tube 71 is arranged to be disposed within the opening 90 in the slider 84. A pair of brackets 93 and 95 are disposed above and beneath the slider 84, respectively. The brackets 93 and 95 extend only partly transversely across the body of the valve housings 56 and 58. A nub 94 is arranged on the lower outside edge of the opening 86 on the front housing 56. A faceplate 96 is disposed on the distalmost end of the slider 84. A spring 98 is disposed between the back side of the faceplate 96 and the nub 94, so as to continuously bias the slider 84 outwardly from the valve 52. The flexible resilient conduit 71 is biased in the pinched closed condition by being pressed against the pair of brackets 93 and 95 on the front half 56 of the housing 54, by the proximalmost wall 92 across the end of the slider 84.

The back half 58 of the housing 54 may have a frangible panel 100 adjacent the slider 84. The panel 100 may have a tab member 102 which extends inwardly towards the center of the valve 52 and near the proximal most wall 103 of the slider 84.

Figure 3:
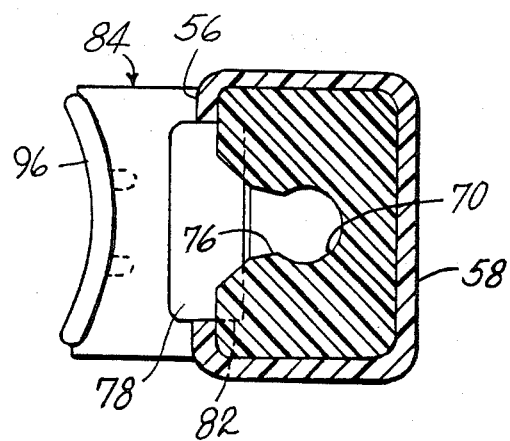
FIG. 3 is a sectional view taken along the lines III—III of FIG. 2.

During use of the urine meter assembly 20, urine is first retained in the receptacle 22 for initial volume measurement thereof. Actual sampling of the urine for further testing will usually be necessary. As is most often the case, only small samples, say in the range of 2 to 10 milliliters are needed. This may be done by inserting a needle with syringe through the septum 78 so as to retrieve the fresh urine which is collected within the bore 70 of the valve 52 at the bottom of the receptacle 22. The needle may be merely inserted through the resealable septum 78 through the orifice 76 and the front portion 74 of the adapter 66 until it reaches the bore 70, whereupon the small sample may be taken. The path for this sampling is also shown in FIG. 3 wherein the septum 78 shows access to the orifice 76 and the bore 70 of the valve 52.

When larger urine samples are required to be taken, such as for specific gravity tests of the urine, wherein 30 to 40 milliliters of fresh urine may need to be removed, the slider 84 may be pressed inwardly against the biasing action of the spring 98 so as to open the flexible tube and unpinch it, thus permitting rapid drainage of the rigid receptacle 22. Unfortunately however, this action may permit the possibility of contamination of the receptacle 22. It is important to utilize the slider 84 for taking urine samples as infrequently as possible. It is also very important to know that a large sample, has been taken when one actually has been done! Thus the valve indicating opening indicating means such as the frangible panel on the back half of the housing 58 may be utilized to show that the slider 84 has been pressed inwardly so as to fracture the frangible panel 100 by pressing against the tab 102 thereof.

A frangible panel would discourage the easy (or lazy) way of taking a small urine sample and make evident the use of such a procedure and indicate the possibility of contamination. The bag or collection system 20 could then be changed or other necessary actions undertaken.

Other slider evident means for valve opening means may be arranged around the valve housing 54 as shown in dashed lines in FIG. 2, such as a heat shrinkable band or tape 110 which may be disposed about the periphery of the valve housing 54 and particularly about the back side of the back half of the housing 58. Thus if the slider 84 were pushed inwardly to open (unpinch) the flexible tubing 71, the tamper evident seal or band 110 would be torn or otherwise disturbed by the back wall 92 of the slider 84, or something in the nature of a boss 105 on the backside to indicate that the valve had been opened for flow of urine samples therethrough.

The need for fresh samples from both the small and large sample sources is significant because if the sample is mixed with older urine, important medical information regarding the ongoing and developing condition of the patient may be lost.

Thus there has been shown a novel arrangement for permitting small fresh samples to be taken from a urine meter, while also permitting larger fresh urine samples to be taken as required before they are otherwise dumped into the main collection bag 24. The large sampler means, however, having utilization discouraging or tamper evident means therewith in order to inhibit medical personnel from taking the small samples from the large sampler means. The more frequently the large samples are taken, the more likely the possibility of contamination within the entire system.

We claim:

1. A multiple use valve assembly having means for permitting only small samples to be taken therefrom and further means for permitting larger samples therefrom, said valve comprising:

a housing having a front portion and a rear portion, said housing having a generally longitudinal opening therethrough;

an intake opening at one end of said housing and a large sample discharge opening at the other end of said housing;

a sealable sampling port for taking small urine samples from said housing, adjacent its intake opening;

a biased release means in said housing adjacent its discharge opening for the discharge of large samples of urine thereby;

a tamper evident means associated with said housing and said biased release means to indicate any discharge of urine through said larger sample means by the use of said biased release means;

an elongated adapter comprising the intake opening of said housing, said elongated adapter having a generally longitudinally directed bore therethrough;

said elongated adapter having said sampling port through a sidewall thereof, said sampling port being in fluid communication with said bore; and a flexible tube secured to the discharge end of said elongated adapter, said flexible tube extending through said biased release means and open at the discharge opening said housing;

said tamper evident means comprising a frangible panel disposed in said rear portion of said housing, in alignment with said biasing means disposed through said front housing, wherein displacement of said biased means so as to undistort said flexible tube to permit the flow of urine therethrough, will fracture said frangible panel in said rear housing, thus indicating the large sampling means' use.

2. A multiple use valve as recited in claim 1, wherein said biased release means extends through an opening in the front portion of said housing, adjacent its large sample discharge opening, said biased release means having a spring which effectuates a constant pressure to close said flexible tube until said means is pressed from the outside.

3. A multiple use valve assembly as recited in claim 2, wherein said biased release means effectuates a distortion in said flexible tube by pinching said tube against the inside of said housing.

4. A multiple use valve assembly as recited in claim 2, wherein said tamper evident means comprises a tearable band disposed about said housing adjacent said biased release means, wherein displacement of said release means will effectuate tearing of said band to indicate use of said biasing means.

5. A multiple use valve assembly as recited in claim 2, wherein said sampling port comprises a septum which may be pierced by a sampling means, which septum reseals itself when said sampling means is withdrawn therefrom.

6. A multiple use valve assembly as recited in claim 2, wherein said biased release means has a back wall which strikes the tamper evident means causing a disturbance thereof, thus indicating its use.

7. A valve assembly for the release of large samples of urine from a urine meter on a urine collection bag, said valve assembly comprising:

a urine collection bag;

a housing having a front portion and a rear portion, said housing having a generally longitudinal channel therethrough;

an intake opening at one end of said housing and a large sample discharge opening of the other end of said housing, said housing being in fluid communication with said urine meter on said urine collection bag;

a biased release means disposed on the front portion of said housing adjacent its discharge opening to permit the discharge of large samples of fresh urine from said urine meter; and frangible tamper evident means arranged on said housing proximal to said biased release means to provide indication of use of said biased release means.

8. A valve assembly as recited in claim 7, wherein said biased release means has a bias means disposed on the front portion of said housing.

9. A valve assembly as recited in claim 7, wherein said tamper evident means comprises a frangible panel disposed on said rear portion of said housing, which frangible panel is struck by said biased release means to indicate its use.

10. A valve assembly as recited in claim 9, wherein said biased release means comprises a slider which is disposed into said housing, said slider having one end which is arranged to strike said frangible panel when said biased release means is utilized.

11. A valve assembly as recited in claim 10, wherein said bias means comprises a spring disposed between the front of said housing and a portion of said slider.

12. A valve assembly as recited in claim 10, including a further sampling means for permitting only small samples of urine to be taken therefrom.

13. A valve assembly as recited in claim 7, wherein said tamper evident means comprises a disturbable band disposed about said housing adjacent said biased release means so as to indicate use thereof if said band is disturbed.

* * * * *